(12) United States Patent
Carrez et al.

(10) Patent No.: US 8,585,650 B2
(45) Date of Patent: Nov. 19, 2013

(54) NEEDLE STICK GUARD, AND PUNCTURING KIT INCLUDING SUCH A NEEDLE STICK GUARD

(75) Inventors: Jean-Luc Carrez, Ecouen (FR); Jean-Louis Coussegal, Beauchamp (FR); Fabien Letang, Morienval (FR); Pierrick Guyomarc'h, Ermont (FR)

(73) Assignee: Vygon (FR)

(*) Notice: Subject to any disclaimer, the term of this patent is extended or adjusted under 35 U.S.C. 154(b) by 26 days.

(21) Appl. No.: 13/503,741

(22) PCT Filed: Oct. 26, 2010

(86) PCT No.: PCT/EP2010/066119
§ 371 (c)(1),
(2), (4) Date: Apr. 24, 2012

(87) PCT Pub. No.: WO2011/051259
PCT Pub. Date: May 5, 2011

(65) Prior Publication Data
US 2012/0209202 A1 Aug. 16, 2012

(30) Foreign Application Priority Data
Oct. 26, 2009 (FR) .................................... 09 57507

(51) Int. Cl.
*A61M 5/32* (2006.01)

(52) U.S. Cl.
USPC .................................................. 604/164.08

(58) Field of Classification Search
USPC .................................................. 604/164.08
See application file for complete search history.

(56) References Cited

U.S. PATENT DOCUMENTS

| | | | | |
|---|---|---|---|---|
| 4,804,371 A | * | 2/1989 | Vaillancourt | 604/198 |
| 5,853,393 A | * | 12/1998 | Bogert | 604/165.02 |
| 2002/0045843 A1 | * | 4/2002 | Barker et al. | 600/585 |
| 2008/0065015 A1 | | 3/2008 | Fiser et al. | |

FOREIGN PATENT DOCUMENTS

| | | |
|---|---|---|
| EP | 0747083 A2 | 12/1996 |
| WO | 0178595 A1 | 10/2001 |
| WO | 2004043521 A1 | 5/2004 |

OTHER PUBLICATIONS

Preliminary Research Report for Application No. FR 0957507 dated May 25, 2010.

* cited by examiner

*Primary Examiner* — Aarti B Berdichevsky
(74) *Attorney, Agent, or Firm* — Lerner, David, Littenberg, Krumholz & Mentlik, LLP

(57) ABSTRACT

The invention relates to a needle stick guard for an anti-needle-stick puncturing kit for positioning a catheter according to the Seldinger technique, including a rocker having a journal so as to enable same to rotate about an axis, and an outer tip for locking the needle stick guard together with a base of another element of the puncturing kit. The rocker comprises three positions: a position in which it is locked together with another element of the puncturing kit; a position in which it is unlocked from the other element of the puncturing kit; and a protection position for trapping a sharp end of a needle in the guard.

10 Claims, 3 Drawing Sheets

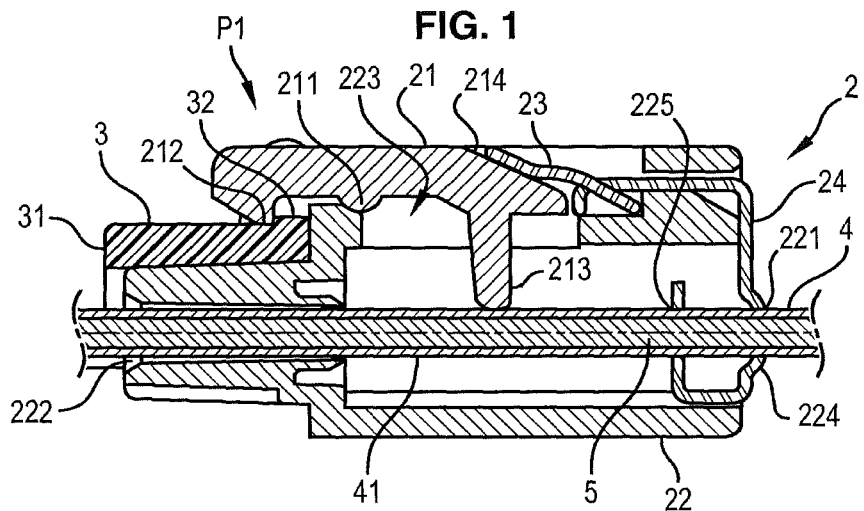
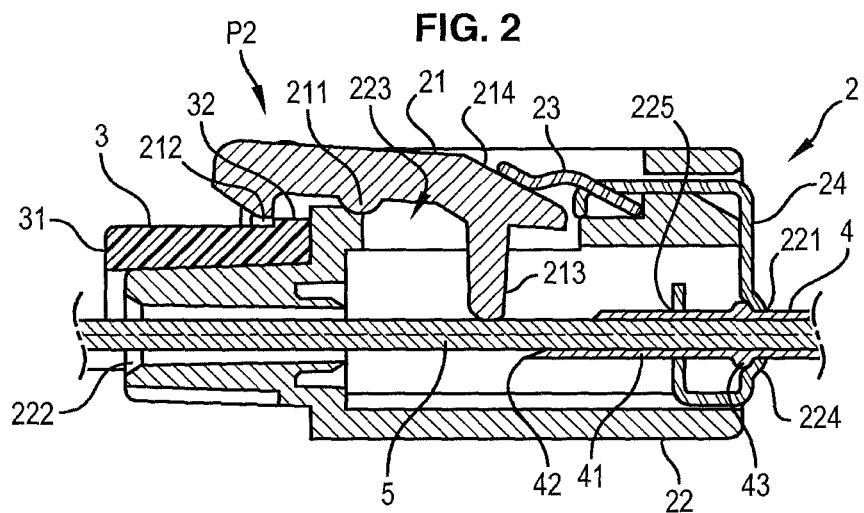
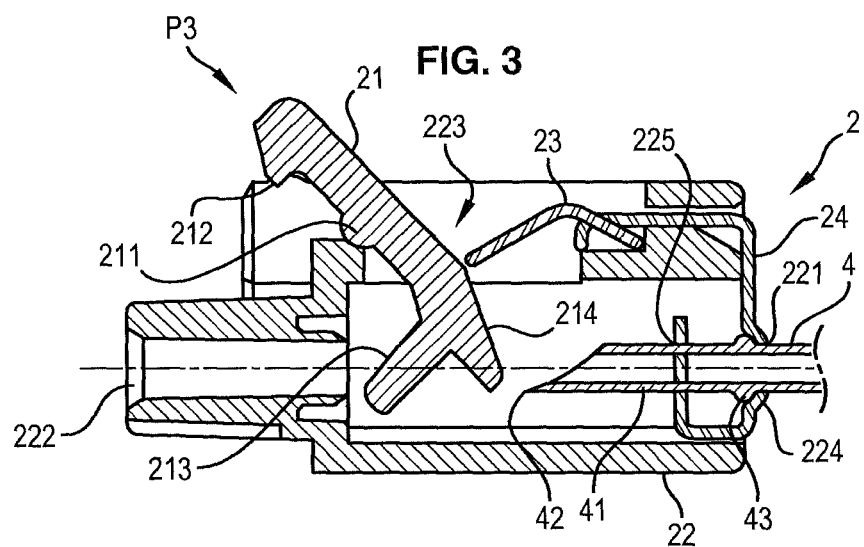

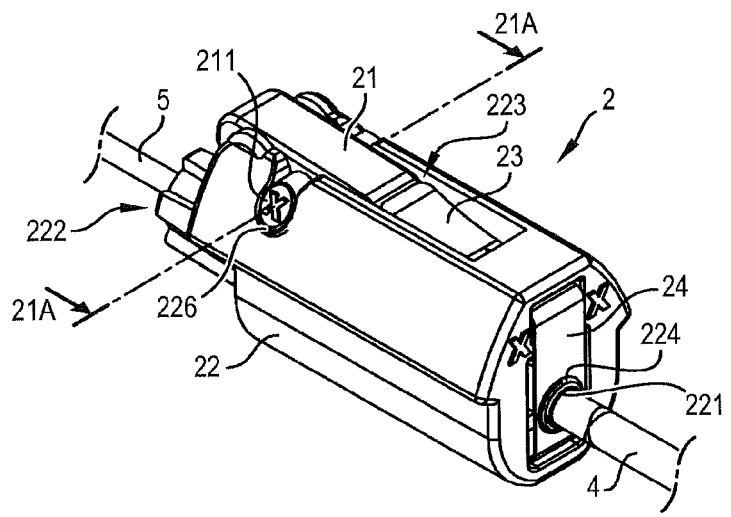
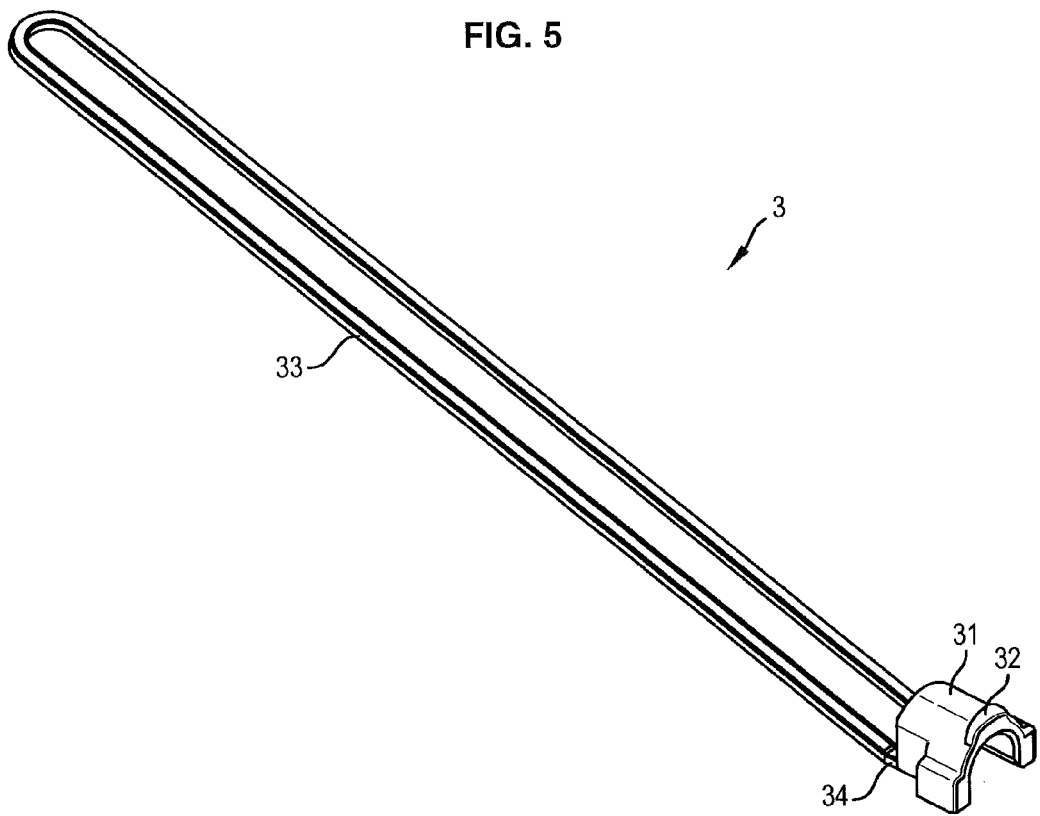

NEEDLE STICK GUARD, AND PUNCTURING KIT INCLUDING SUCH A NEEDLE STICK GUARD

CROSS-REFERENCE TO RELATED APPLICATIONS

The present application is a national phase entry under 35 U.S.C. §371 of International Application No. PCT/EP2010/066119 filed Oct. 26, 2010, published in French, which claims priority from FR 0957507 filed Oct. 26, 2009, all of which are incorporated herein by reference.

BACKGROUND OF THE INVENTION

The invention relates to a needle stick guard for an anti-needle-stick puncturing kit for installing a catheter by the Seldinger method.

The invention also relates to an anti-needle-stick puncturing kit for installing a catheter by the Seldinger method.

STATE OF THE ART

The Seldinger method is a method for installing a central catheter intravenously with its distal end at the aorta. This method also allows an artery to be catheterized.

The installation of a catheter by the Seldinger method comprises the following steps: insertion of the needle into a vein up to the desired location; insertion of a guide within the needle up to the desired location; withdrawal of the needle from the vein, the guide remaining in place; insertion of a catheter by sliding along the guide up to the desired location; and withdrawal of the guide.

It is possible, between the needle withdrawal step and that of inserting the catheter, to widen the incision made by the needle in the skin by inserting, by sliding along the guide, a dilator known to those skilled in the art. Once the incision is enlarged, the dilator is withdrawn, the guide remaining in place.

Handling a needle during the installation of a catheter by the Seldinger method carries a risk of injury to the operator.

BRIEF SUMMARY OF THE INVENTION

One object of the invention is to correct at least one disadvantage of the state of the art.

To this end, the invention proposes a needle stick guard for an anti-needle-stick puncturing kit for installing a catheter by the Seldinger method, comprising:
a rocker having a bearing allowing its rotation about an axis, and an external tip for locking the needle stick guard together with a base of another element of the puncturing kit; a body comprising: a proximal hole and a distal hole for inserting a tube of a needle and inserting a spiral guide between the proximal and distal holes; a slot for accommodating the rocker; and a housing on the periphery of the slot for receiving the bearing of the rocker; Characterized in that the rocker has three positions: a locking position wherein the external tip locks the needle stick guard together with the base of the other element of the puncturing kit; an unlocking position wherein the external tip releases the needle stick guard from the other element of the puncturing kit; and a protection position wherein the sharp end of the needle is trapped by the body of the rocker; and in that the rocker has a spur within the body for controlling the position of the rocker with respect to an outside diameter of the needle tube and/or of the spiral guide; the locking position being obtained when the spur rests on the needle tube; the unlocking position being obtained when the spur rests on the spiral guide; and the protection position being obtained when the spur rests neither on the needle tube nor on the spiral guide.

Other optional and non-limiting features are: the guard also includes a resilient element to force the rocker toward the interior of the guard body; the proximal hole has a diameter fitted to the diameter of the needle tube; the proximal hole is made in a metal strip, the metal strip and the resilient element constituting a single part; the guard also includes an indentation extending outward with respect to the body and surrounding the proximal hole for receiving a local distortion of the needle tube; and the guard also has an intermediate hole between the proximal hole and the distal hole for stabilizing the needles with respect to the needle stick guard.

The invention also proposes an anti-needle-stick puncturing kit for installing a catheter by the Seldinger method at a catheterization point on the skin of a living being comprising: a needle stick guard according to one of the embodiments of the invention; an immobilizing element for temporarily immobilizing the needle stick guard in proximity to the catheterization point; the immobilization element comprising a base for receiving the distal portion of the needle stick guard and a ridge arranged on the base and designed to be seized by the outer tip of the needle stick guard.

Other optional and non-limiting features are: the immobilization element also includes a longitudinal element connected to the base by a hinge for moving the longitudinal element between a proximal position and a distal position; the longitudinal element being in contact with the skin in its distal position and allowing the temporary immobilization of the anti-needle stick guard by its attachment to the skin; the puncturing kit also includes a connector comprising: a guard housing for receiving a proximal portion of the needle stick guard; and a needle housing for receiving a base of the needle; the needle housing including means of connecting with the base of the needle; the guard housing of the connector is a slot fitted to the needle stick guard so as to block rocker in the locking position when the needle stick guard is lodged in the guard.

An advantage of the needle stick guard and of the anti-needle-stick puncturing kit according to the invention is to allow operation of the puncturing kit without needle stick risk to the operator, without adding supplementary and constraining operations.

BRIEF DESCRIPTION OF THE DRAWINGS

Other features, goals and advantages will appear upon reading the following detailed description, with reference to the drawings provided by way of illustration and without limitation, among which:

FIG. 1 is a longitudinal section view of an needle stick guard according to the invention, and showing the guard in a first configuration;

FIG. 2 is a longitudinal section view of the needle stick guard of FIG. 1, and showing the guard in a second configuration;

FIG. 3 is a longitudinal section view of the needle stick guard of FIG. 1, and showing the guard in a third configuration;

FIG. 4 is a three-quarters view of the needle stick guard of FIG. 1;

FIG. 5 is a three-quarters view of an immobilization element used with the needle stick guard of FIG. 1;

DETAILED DESCRIPTION OF THE INVENTION

Figure 6:
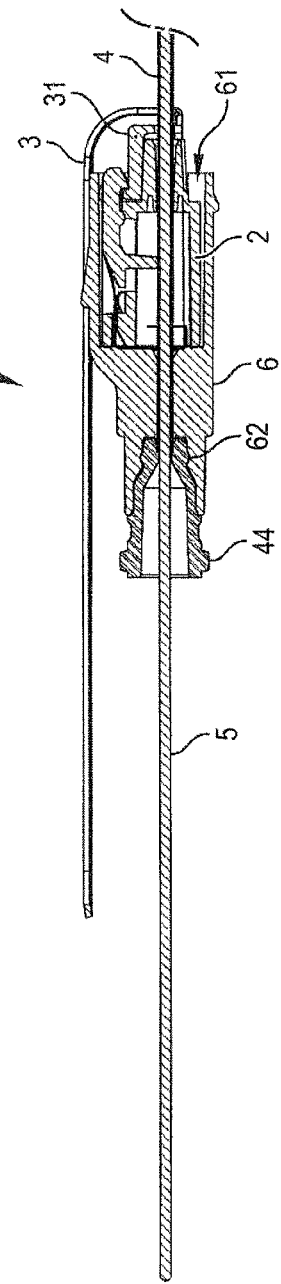
FIG. 6 is a longitudinal section view of an anti-needle-stick puncturing kit according to the invention with an immobilization element in its proximal position.
Figure 7:
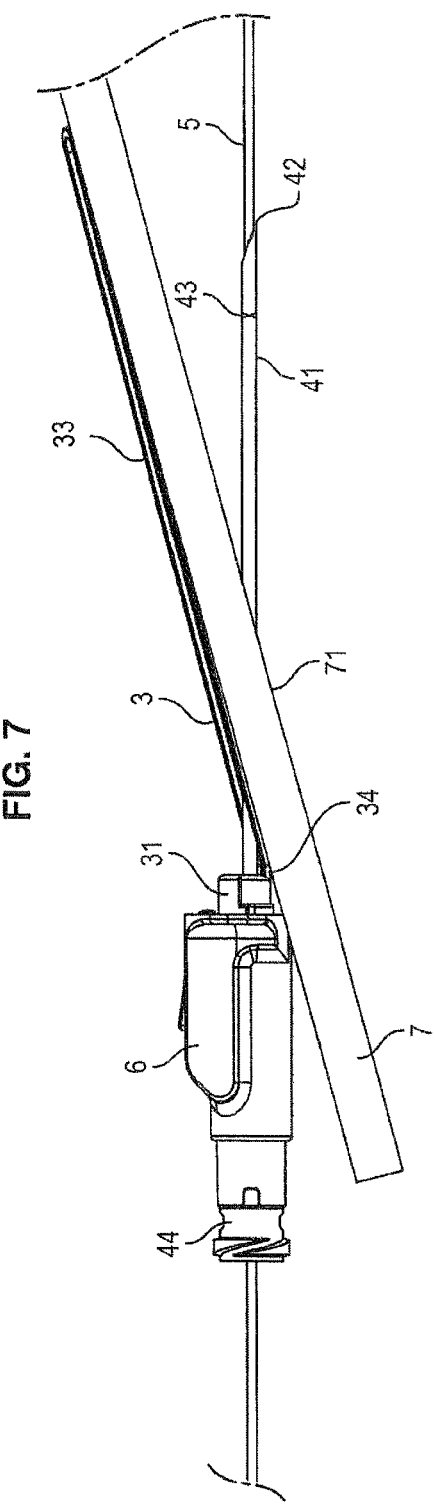
FIG. 7 is a profile view of the anti-needle-stick puncturing kit of FIG. 6 with the immobilization element in its distal position, in contact with the skin of a living being.

An anti-needle-stick puncturing kit and a needle stick guard for the anti-needle-stick puncturing kit for installing a catheter by the Seldinger method are described hereafter with reference to FIGS. 1 through 7.

The anti-needle-stick puncturing kit 1 according to the invention includes a needle stick guard 2.

In the rest of the detailed description, the adjectives "proximal" and "distal" designate positions relative to one another. The proximal position is that which is closer to the body of the operator holding the needle stick guard 2. The distal position is that which is farther from the body of the operator holding the needle stick guard 2.

The needle stick guard 2 includes a body 22 including a proximal hole 221 and a distal hole 222 for the insertion of a tube 41 of a needle 4 and the insertion of a spiral guide 5 between the proximal 221 and distal 222 holes.

The body 22 also includes a slot 223 for receiving a rocker 21, and a housing 224 at the periphery of the slot 223 for receiving a bearing 211 of the rocker 21.

The needle stick guard 2 therefore includes a rocker 21 having a bearing 211 for its rotation about an axis 21 A, and an external tip 212 for locking the needle stick guard 2 together with a base 31 of another element of the puncturing kit 1.

The other element can for example be an immobilization element 3 of the needle stick guard 2 described later in greater detail.

The other element can be any other element which needs to be locked together with the needle stick guard 2.

The rocker 21 exhibits three distinct positions, P1, P2, P3 about its axis of rotation 21 A.

A locking position P1 is shown in FIG. 1.

In this locking position P1, the external tip 212 locks needle stick guard 2 together with the base 31 of the other element 3 of the puncturing kit 1.

An unlocking position P2 is shown in FIG. 2.

In this unlocking position P2, the external tip 212 releases the needle stick guard 2 from the other element 3 of the puncturing kit 1.

A protection position P3 is shown in FIG. 3.

In this protection position P3, the sharp end 42 of the needle 4 is trapped by the body 22 and the rocker 21.

In order to control the position of the rocker 21 about its axis of rotation 21 A, the rocker 21 has a spur 213 within the body 22. The spur 213 therefore extends into the slot 223.

Control of the position of the rocker 21 about its axis of rotation 21A is carried out with respect to an outside diameter of the tube 41 of the needle 4 and/or of the spiral guide 5. In greater detail, the spur 213, the outside diameter of the tube 41 of the needle 4 and the diameter of the spiral guide 5 cooperate in such a way that: the locking position P1 is obtained when the spur 213 is resting on the outer diameter of the tube 41 of the needle 4; the unlocking position P2 is obtained when the spur 213 is resting on the outer diameter of the spiral guide 5; and the protection position P3 is obtained when the spur 213 is resting neither on the outer diameter of the tube 41 of the needle 4 nor on that of the spiral guide 5.

The arrangement of a rocker 21 having these three positions is advantageous for an anti-needle-stick puncturing kit 1 having in addition, for example, an immobilization element 3 to temporarily immobilize the needle stick guard 2 in proximity to a catheterization point 71 made on the skin 7 of a living being.

The immobilization element 3 allows the needle stick guard 2 to be temporarily held immobile. Thus, upon withdrawal of the needle 4 along the needle stick guard 2, this makes it possible to prevent the needle stick guard 2 from being dragged along by the withdrawal motion of the needle 4.

This is important for bringing the sharp end 42 of the needle 4 into the needle stick guard 2.

The immobilization element 3 can include a base 31, for receiving a distal portion of the needle stick guard 2, and a ridge 32 arranged on the base 31. This ridge 32 is designed to be seized by the external tip 212 of the needle stick guard 2; the seizing of the ridge 32 with the external tip 212 allowing the needle stick guard 2 to be locked together with the immobilization element 3.

During the installation of a catheter by the Seldinger method, the puncturing kit 1 is used as follows.

First of all, the needle 4, the tube whereof is already inserted between the proximal hole 221 and the distal hole 222 of the needle stick guard 2, is inserted through the skin 7 at the catheterization point 71 using its sharp end 42. Upon insertion of the needle 4, the puncturing kit 1 is brought close to the skin 7 up to the catheterization point 71.

The external tip 212 is seizing the ridge 32. For example, the external tip 212 constitutes a stop for the ridge 32: the immobilization element 3 cannot be separated from the needle stick guard 2 as illustrated in FIG. 1 (also showing the spiral guide 5 already inserted; see below).

Once the needle 4 is in place, the spiral guide 5 is inserted inside the 4 needle (and therefore through the needle stick guard 2) up to the desired location within a vein or an artery. The needle 4 must then be withdrawn, while the needle stick guard 2 must remain in place: this is made possible thanks to the immobilization element 3.

For example, as illustrated in FIG. 5, the immobilization element 3 also includes a longitudinal element 33 connected to the base 31 by a hinge 34 for moving the longitudinal element 33 between a proximal position and a distal position.

When the spiral guide 5 is inserted into the needle 4 (in the direction leading from the proximal hole 221 toward the distal hole 222) and set in place, the longitudinal element 33, initially folded over toward the needle stick guard 4 (in its proximal position), is brought into contact with the skin 7 in its distal position. Its attachment to the skin 7 allows the immobilization of the needle stick guard 2 because it is locked together with the immobilization element 3.

The attachment of the longitudinal element 33 can be provided either by simple pressure of the longitudinal element 33 on the skin 7 (pressure applied by the operator's hand), or by the use of an adhesive (adhesive plaster or other), or by any other suitable means.

During withdrawal of the needle 4 (in the direction leading from the distal hole 222 toward the proximal hole 221), the spur 213 of the rocker rests on the outer diameter of the tube 41 of the needle 4. The needle stick guard 2 is therefore locked together with the immobilization element 3.

When the needle is withdrawn sufficiently, the spur 213 no longer rests on the outer diameter of the tube 41 of the needle 4, but rather on the outer diameter of the spiral guide 5

(unlocking position P2, see FIG. 2): the rocker has then undergone a rotation about its axis of rotation 21 A due to its weight.

This rotation of the rocker 21 can also be provided for thanks to a resilient element 23 provided on the needle stick guard 2 to force the rocker 21 toward the inside of the body 22 of the guard 2.

For example, the rocker 21 has a contact surface 214 and the resilient element 23, which can be a strip of metal, presses on the contact surface 214 so as to exert a force toward the inside of the slot 223.

The force exerted is weak enough that the needle 4 can easily be moved by sliding between the distal hole 222 and the proximal hole 221, and that later, during withdrawal of the needle stick guard 2 when the spur 213 is resting on the spiral guide 5, the spiral guide 5 is not dragged along. But the force exerted must be greater than the weight of the rocker 21 and greater than the friction forces between the bearing 211 and its housing 224.

The rotation of the rocker 21 causes the external tip 212 to lift, releasing the ridge 32: the ridge 32 no longer abutting the external tip 212, the needle stick guard 2 can be moved away from the immobilization element 3.

The needle stick guard 2 is moved away from the immobilization element 3 by the operator by continuing to pull on the needle 4 in the manner known to those skilled in the art.

For example the proximal hole 221 of the needle stick guard 2 has a diameter fitted to the diameter of the tube 41 of the needle 4 and the tube 41 of the needle 4 has a local distortion 43 so that the tube 41 has, in at least one direction, dimensions greater than the diameter of the proximal hole 221. For example, the tube 41 is flattened at one spot.

The distance between the sharp end 42 and the local distortion 43 is selected so that the sharp end 42 remains inside the needle stick guard 2 when the spur 213 of the rocker 21 is no longer in contact with the outer diameter of the tube 41 of the needle 4, and so as to make possible the rotation of the rocker 21 about its axis of rotation 21 A toward its protection position P3.

The operator then continues to withdraw the needle 4, drawing the needle stick guard 2 away from the immobilization element 3 until the spiral guide 5 is completely disengaged from the needle stick guard 2: the spur 213 no longer resting on the outer diameter of the spiral guide 5.

When the spur 213 no longer rests on the outer diameter of the spiral guide 5, the rocker 21 undergoes a rotation about its axis of rotation 21 A toward the inside of the slot 223 due to its weight and/or possibly due to the resilient element 23 toward its protection position P3 as illustrated in FIG. 3.

In the protection position P3 the rocker prevents the sharp end 42 from re-emerging from the needle stick guard 2 as a result of a movement of the needle 4 in the direction leading from the proximal hole 221 toward the distal hole 222. The movements of the needle 4 can therefore be constrained thanks to the rocker 21, on the one hand, and the local distortion 43 of the tube 41 of the needle 4.

When the needle stick guard 2 includes the resilient element 23, the fact that it is selected so that the force that it exerts on the contact surface 214 of the rocker 21 is greater than the weight 21 makes it possible to prevent the rocker 21 from leaving the slot 223 if the needle stick guard 2 happens to be turned over.

Operationally, the proximal hole 221 can be made in a metal strip 24, the metal strip 24 and the resilient element 23 forming a single part.

Thus when the operator withdraws the needle 4 in the direction leading from the distal hole 222 toward the proximal hole 221, the local distortion 43 of the tube 41 of the needle 4 comes into abutment against the periphery of the proximal hole 221 and deforms the metal strip 24. The deformation of the metal strip 24 brings about the application of an additional force by the resilient element 23 on the contact surface 214 of the rocker 21 that further favors the rotation of the rocker 21 about its axis of rotation 21 A.

The needle stick guard 2 can also include, in the cases where the proximal hole 221 is fitted to outside diameter of the tube 41 of the needle 4, an indentation 224 extending outward with respect to the body 22 and surrounding the proximal hole 221 for receiving the local distortion 43 of the tube 41 of the needle 4.

The needle stick guard 2 can also include an intermediate hole 225 between the proximal hole 221 and the distal hole 222 for stabilizing the needle 4 with respect to the needle stick guard 2.

The position of the intermediate hole 225 is selected so as to position it between the proximal hole 221 and the rocker 21 when it is in its protection position P3, the tube 41 of the needle 4 then passing through the proximal hole 221 and the intermediate hole 225.

The anti-needle-stick puncturing kit 1 can also include a connector 6 comprising: a guard housing 61 for receiving a proximal portion of the needle stick guard 2; and a needle housing 62 for receiving a base 44 of the needle 4.

Thus, thanks to this connector 6, the mounting of the needle 4 in the needle stick guard 2 is easier. The handling of the needle is also facilitated, since the operator can handle the connector 6, the dimensions whereof being selected to be larger than those of the base 44 of the needle 4. Indeed, during withdrawal of the needle 4, the operator handles the connector 6.

The needle housing 62 includes means for connecting with the base 44 of the needle 4, for example a Luer type recess.

The guard housing 61 of the connector 6 can be a recess fitted to the needle stick guard 2 so as to block the rocker 21 in the locking position P1 when the needle stick guard 2 is housed in the guard housing 61.

The base 44 of the needle 4 can have a funnel (of the Luer type for example) that eases the insertion of the spiral guide 5.

The invention claimed is:

1. A needle stick guard for an anti-needle-stick puncturing kit for installing a catheter by the Seldinger method, comprising:
    a rocker having a bearing for its rotation about an axis, and an external tip for locking the needle stick guard together with a base of another element of the puncturing kit;
    a body comprising:
        a proximal hole and a distal hole for inserting a tube of a needle and inserting a spiral guide between the proximal and distal holes;
        a slot for receiving the rocker; and
        a housing on the periphery of the slot for receiving the bearing of the rocker;
    characterized in that the rocker has three positions about its axis of rotation:
    a locking position wherein the external tip locks the needle stick guard together with the base of the other element of the puncturing kit;
    an unlocking position wherein the external tip releases the needle stick guard from the other element of the puncturing kit; and
    a protection position wherein the sharp end of the needle is trapped by the body of the rocker;

and in that the rocker has a spur within the body for controlling the position of the rocker with respect to an outer diameter of the tube of the needle and/or of the spiral guide;

the locking position being obtained when the spur is resting on the tube of the needle;

the unlocking position being obtained when the spur is resting on the spiral guide; and the protection position being obtained when the spur is resting neither on the tube of the nor on the spiral guide.

2. A needle stick guard according to claim 1, further comprising an intermediate hole between the proximal hole and the distal hole for stabilizing the needle with respect to the needle stick guard.

3. A needle stick guard according to claim 1, further comprising a resilient element for forcing the rocker toward the inside of the body of the guard.

4. A needle stick guard according to claim 3, wherein the proximal hole is made in a metal strip, the metal strip and the resilient element constituting a single element.

5. A needle stick guard according to claim 1, wherein the proximal hole has a diameter corresponding to the diameter of the tube of the needle.

6. A needle stick guard (2) according to claim 5, further comprising an indentation, which protrudes from the body and surrounds the proximal hole, for receiving a local distortion of the tube of the needle.

7. An anti-needle-stick puncturing kit for installing a catheter by the Seldinger method at a catheterization point on the skin of a living being, comprising:

a needle stick guard according to claim 1;

an immobilization element for temporarily immobilizing the needle stick guard close to the catheterization point;

the immobilization element including a base for receiving a distal portion of the needle stick guard and a ridge arranged on the base and adapted to be seized by the external tip of the needle stick guard.

8. An anti-needle-stick puncturing kit according to claim 7, wherein the immobilization element further comprises a longitudinal element connected to the base by a hinge for moving the longitudinal element between a proximal position and a distal position;

the longitudinal element being in contact with the skin in its distal position and allowing a temporary immobilization of the needle stick guard by attaching it to the skin.

9. An anti-needle-stick puncturing kit according to claim 7, further comprising a connector comprising:

a guard housing for receiving a distal portion of the needle stick guard; and a needle housing for receiving a base of the needle;

the needle housing including means for connecting with the base of the needle.

10. An anti-needle-stick puncturing kit according to claim 9, wherein the guard housing of the connector comprises a recess fitted to the needle stick guard so as to block the rocker in the locking position when the needle stick guard is housed in the guard housing.

* * * * *

UNITED STATES PATENT AND TRADEMARK OFFICE
CERTIFICATE OF CORRECTION

PATENT NO. : 8,585,650 B2  
APPLICATION NO. : 13/503741  
DATED : November 19, 2013  
INVENTOR(S) : Jean-Luc Carrez et al.

Page 1 of 1

It is certified that error appears in the above-identified patent and that said Letters Patent is hereby corrected as shown below:

In the Claims

Column 7, line 24, Claim 6, delete "(2)".

Signed and Sealed this  
Twenty-third Day of June, 2015

Michelle K. Lee  
*Director of the United States Patent and Trademark Office*